United States Patent
Niggl et al.

(10) Patent No.: US 7,123,398 B2
(45) Date of Patent: Oct. 17, 2006

(54) ARRANGEMENT AND USE OF A SLIT DIAPHRAGM

(75) Inventors: Lutz Niggl, Salzburg (AT); Karl Puchegger, Ternitz (AT)

(73) Assignee: Tecan Trading AG, Maennedorf (CH)

( * ) Notice: Subject to any disclaimer, the term of this patent is extended or adjusted under 35 U.S.C. 154(b) by 5 days.

(21) Appl. No.: 10/889,650

(22) Filed: Jul. 12, 2004

(65) Prior Publication Data

US 2005/0030607 A1    Feb. 10, 2005

(30) Foreign Application Priority Data

Jul. 14, 2003    (CH)    ..................... 01230/03

(51) Int. Cl.
*G02B 26/02*    (2006.01)

(52) U.S. Cl. .................. 359/232; 359/739; 356/310

(58) Field of Classification Search ............... 359/227, 359/232–233; 356/300, 310, 326, 329–332
See application file for complete search history.

(56) References Cited

U.S. PATENT DOCUMENTS

| | | | | |
|---|---|---|---|---|
| 48,442 | A * | 6/1865 | Xiao ............................ | 68/101 |
| 4,641,938 | A * | 2/1987 | Lazzati ........................ | 396/482 |
| 5,233,405 | A * | 8/1993 | Wildnauer et al. .......... | 356/333 |
| 5,627,671 | A | 5/1997 | Yamura et al. | |
| 5,885,531 | A | 3/1999 | Heffelfinger et al. | |
| 5,969,853 | A * | 10/1999 | Takaoka ..................... | 359/370 |
| 6,310,342 | B1 * | 10/2001 | Braunstein et al. ......... | 250/306 |
| 6,336,752 | B1 * | 1/2002 | Balopole et al. ............ | 396/459 |

FOREIGN PATENT DOCUMENTS

| | | |
|---|---|---|
| EP | 0 482 765 | 4/1992 |
| GB | 2 084 758 | 4/1982 |
| JP | 60039533 | 1/1985 |

OTHER PUBLICATIONS

KRiegsmaterialverwa, Cameral Shutter mechanism- uses two coaxial,Jun. 30, 1976, CH 5771783A, , Abstract and Fig 2.*

* cited by examiner

*Primary Examiner*—Euncha P. Cherry
(74) *Attorney, Agent, or Firm*—Notaro & Michalos P.C.

(57) ABSTRACT

Device (1) and method for delimiting a field (3) impinged with light from a light source (2), particularly on the surface of an optical element (4) and/or sample (5), having a slit diaphragm (6) including a slit height (7) and a slit width (8), which includes first and second linearly movable slides (9, 9'), positioned parallel to one another on two separate parallel lines, which are movable at least partially symmetrically to one another in relation to an optical axis (10), each of the two slides (9, 9') including at least one optical opening (11, 11'), which—for continuous adjustment of at least the slit height (7) or the slit width (8)—may be positioned at least partially on the optical opening (11', 11) of the neighboring slide (9', 9) in the region of the optical axis (10). The device (1) according to the present invention and the method according to the present invention are distinguished in that the device (1) includes a motor drive (15) having an axis of rotation (16) for moving the two slides (9, 9') in a movement direction (19), this axis of rotation (16) of the motor drive (15) being positioned perpendicularly to this movement direction (19).

24 Claims, 3 Drawing Sheets

US 7,123,398 B2

ARRANGEMENT AND USE OF A SLIT DIAPHRAGM

CROSS-REFERENCE TO RELATED APPLICATIONS

This application claims priority of the Swiss patent application No. CH 1230/03 filed on Jul. 14, 2003.

TECHNICAL FIELD OF THE INVENTION

The present invention relates to a device for delimiting a field impinged with light from a light source, particularly on the surface of an optical element and/or sample, having a slit diaphragm including a slit height and a slit width, which includes first and second linearly movable slides positioned parallel to one another on two separate parallel lines, which are movable at least partially symmetrically to one another in relation to an optical axis, each of the two slides including at least one optical opening which may be positioned at least partially on the optical opening of the neighboring slide in the region of the optical axis for continuous adjustment of at least the slit height or the slit width. In addition, the present invention relates to systems for measuring the fluorescence and/or luminescence and/or absorption of samples irradiated with light from a light source, the system including at least one monochromator or a spectrometer having optical elements.

Such systems are known as fluorometers for standard microplates, for example, and have the following optical arrangement: the irradiation direction is vertical and the detector is located on the same optical axis. In this way, light penetrating a sample and/or triggered by a sample and/or reflected or scattered by a sample is detected. Devices which detect penetrating light are called photometers. Devices which detect scattered light are called nephelometers. Fluorometers only detect the light triggered by the sample. Devices which measure the absorption of a substance and/or a solution over a specific wavelength range are called spectrometers and/or spectrophotometers. Devices which measure the fluorescence of a substance and/or a solution over a specific wavelength range are called spectral fluorometers, for example. Measurement systems which combine several of these measurement devices are called multifunction readers, for example.

Typically, spectrometers have slit diaphragms which have a settable and/or variable slit width for selecting a specific wavelength range (bandwidth).

RELATED PRIOR ART

According to an achievement of the object known from the related art (cf. FIG. 1), the slit width is set using a micrometer screw (vertical arrow), which deforms a ring in a targeted way (horizontal double arrow), on which two wedges pointing to one another may be moved away from (as shown) or toward one another. This known achievement of the object, in which the slides defining the slit are located in a line, has the advantage that very small slit widths may be set extremely precisely. However, it has the disadvantage that a costly and complex mechanism must be provided for changing the slit width.

A further achievement of the object from the related art includes inserting and/or changing fixed apertures having defined slit widths and/or slit heights. This achievement of the object is also costly and does not allow continuous adjustment of the slit width.

A device according to the species having two slides is known from GB 2,084,758. This device has a very complex construction and is accordingly costly to manufacture.

OBJECTS AND SUMMARY OF THE INVENTION

The object of the present invention is to suggest alternative and, if possible, simpler achievements of the object for continuous adjustment of the slit height and/or the slit width of slit diaphragms or apertures.

This object is achieved according to a first aspect by the features of the invention, in that the device has a motor drive having an axis of rotation for moving the two slides in a movement direction, this axis of rotation of the motor drive being positioned perpendicularly to this movement direction.

This object is achieved according to second aspect by the features of the invention, in that a corresponding method is suggested for delimiting a field impinged with light from a light source, particularly on the surface of an optical element and/or a sample, in which a device having a slit diaphragm, whose slit height and/or slit width are continuously adjustable, is used. In the method according to the present invention, the slit width of the slit diaphragm is set using first and second sliders positioned parallel to one another on two separate parallel lines, in that these two slides are moved linearly at least partially symmetrically to one another in relation to an optical axis until a desired slit is obtained through at least partial overlap of optical openings positioned in each slide in the region of the optical axis.

Preferred embodiments and further features according to the present invention each result from the dependent claims.

ADVANTAGES OF THE PRESENT INVENTION INCLUDE THE FOLLOWING:

A simple mechanism is suggested, which allows systems for measuring the fluorescence and/or luminescence and/or absorption of samples irradiated with the light from a light source—particularly multifunction readers having multiple such slit diaphragms—to be manufactured more cost-effectively.

The slit width and/or slit height may be changed practically continuously at any time, i.e., even during the irradiation of a sample.

The slit width may also be changed automatically or tailored to a specific sample behavior, in accordance with preset parameters.

BRIEF DESCRIPTION OF THE DRAWINGS

The present invention will now be explained in greater detail on the basis of schematic drawings, which are merely to illustrate exemplary embodiments and are not to restrict the scope of the present invention.

FIG. 2 shows a front view of a slit diaphragm according to the present invention in a first embodiment, having two slides positioned on two separate parallel lines for varying the slit width or the slit height:

DETAILED DESCRIPTION OF THE INVENTION

Figure 1:
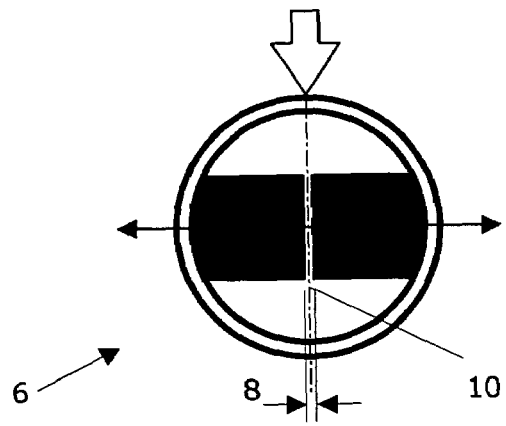
FIG. 1 shows a front view of a variable slit diaphragm known from the related art having two slides positioned together on one line.
Figure 2A:
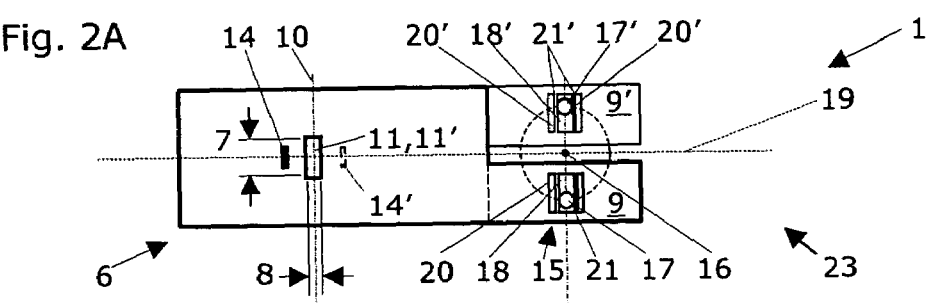
FIG. 2A showing a first slide position, in which the two slides are essentially congruent and define a maximum slit width at a first slit height.
Figure 2B:
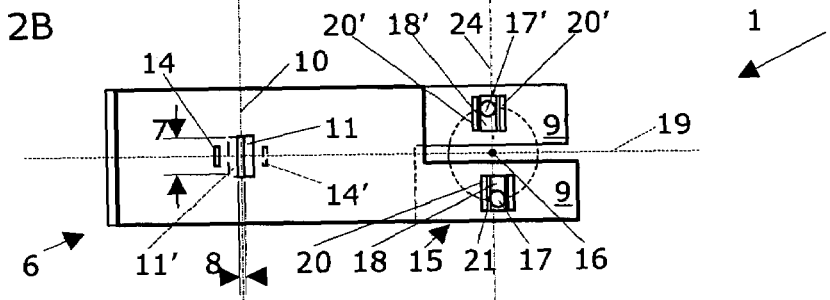
FIG. 2B showing a second slide position, in which the two slides are moved somewhat toward one another, so that a middle slit width at a first slit height results.
Figure 2C:
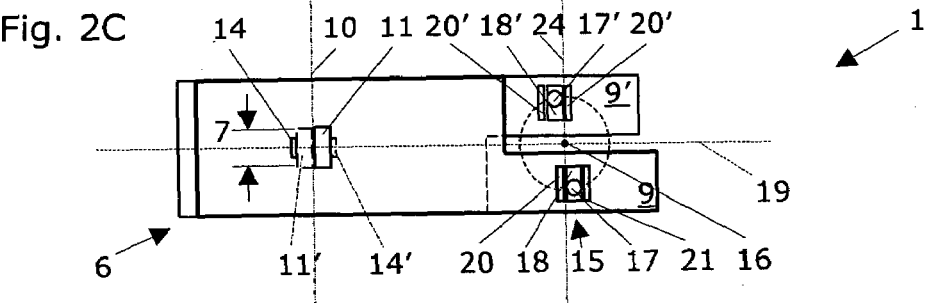
FIG. 2C showing a third slide position, in which the two slides are moved more toward one another, so that a minimum slit width at a first slit height results.
Figure 2D:
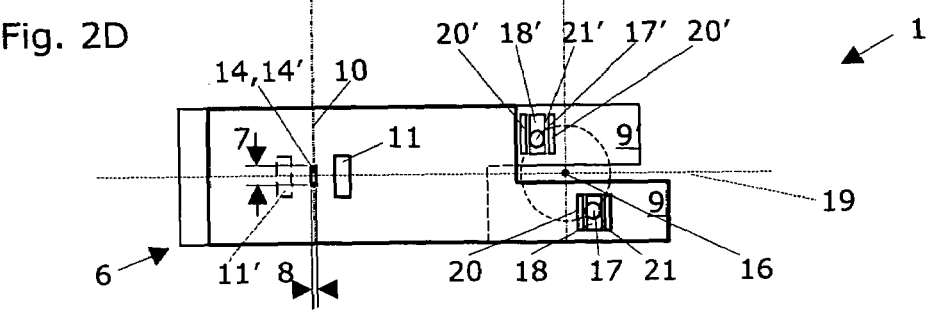
FIG. 2D showing a fourth slide position, in which the two slides are moved further toward one another, so that a fixed slit width having a second, reduced slit height results.

FIG. 1 shows a front view of a variable slit diaphragm 6 known from the related art, having two slides positioned jointly on one line. The slit width 8 is set using a micrometer screw (vertical arrow), which deforms an elastic ring in a targeted way (horizontal double arrow), on which two wedges pointing toward one another may be moved away from (as shown) or toward one another symmetrically in relation to an optical axis 10.

Figure 5:
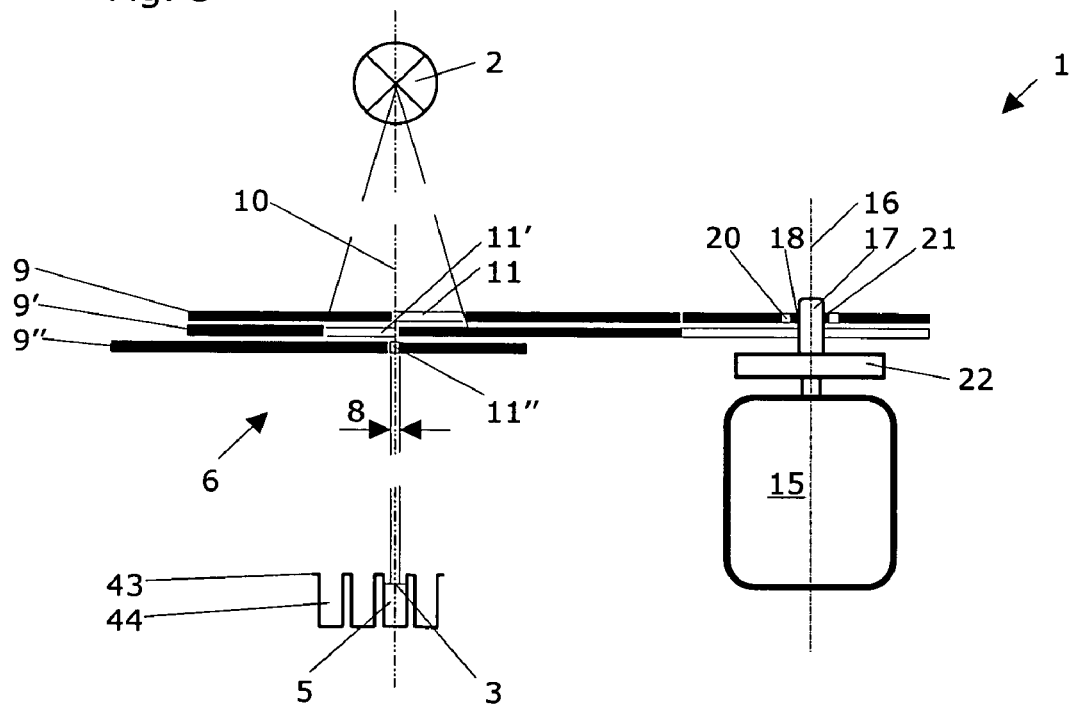
FIG. 5 shows a sectional illustration of a slit diaphragm according to the present invention in a fourth embodiment, having three slides positioned on three separate parallel lines as shown in FIG. 3 in a first slide position, in which the two slides are essentially congruent to one another and define a specific slit width at a maximum slit height.

FIG. 2, in its various sections FIGS. 2A to 2D, shows a front view of a slit diaphragm according to the present invention in a first embodiment, having two slides positioned on two separate parallel lines for varying the slit width or the slit height. A device 1 is shown for delimiting a field 3 (cf. FIGS. 5 and 6) impinged by light from a light source 2 (cf. FIG. 5), particularly on the surface of an optical element 4 (FIG. 6) and/or a sample 5 (FIG. 5). Optical elements 4 include all typical optical components, such as gratings, mirrors, fiber-optic cables, lenses, and the like. Samples 5 include fluids, such as solutions, suspensions, and liquid-gas mixtures, as well as solids, such as emulsions, tissue sections, and cell cultures. The device 1 includes a slit diaphragm 6 having a slit height 7 and a slit width 8, the slit width 8 and/or the slit height 7 being continuously adjustable. The device 1 according to the present invention is distinguished in that the slit diaphragm 6 has first and second linearly movable sliders 9, 9', positioned parallel to one another on two separate parallel lines, which are movable at least partially symmetrically to one another in relation to an optical axis 10. In this case, each of the two slides 9, 9' includes at least one optical opening 11, 11', which may be positioned at least partially on the optical opening 11', 11 of the neighboring slide 9', 9 in the region of the optical axis 10.

According to a first embodiment of the device 1, the optical openings 11, 11' in the two slides 9, 9' have identical, rectangular shapes to produce a variable slit width 8 at a constant slit height 7.

In a first slide position 23 (cf. FIG. 2A), the two slides 9, 9' are essentially congruent to one another and define a maximum slit width 8 at a first slit height 7, which correspond precisely to the dimensions of the optical openings 11, 11'. These optical openings 11, 11' are positioned symmetrically to the optical axis 10 here. The slides 9, 9' include further optical openings 14, 14' which are positioned diametrically opposing at a distance to the optical openings 11, 11' and preferably define a reduced slit height and a specific slit width. As an alternative to the illustration in FIG. 2, the further optical openings 14, 14' may also define a round slit (cf. FIG. 4) or any other geometric surface.

In the movement direction 19, which is shown as the axis of symmetry, these slides 9, 9' are movable using a motor drive 15 (cf. FIG. 5). The axis of rotation 16 of the motor drive 15 for moving the two slides 9, 9' is perpendicular to this movement direction 19, shown as the axis of symmetry. The motor drive 15 includes two movement journals 17, 17', pivotable symmetrically around the axis of rotation 16, each of which engages in a first mechanical opening 18, 18' in the two slides 9, 9'. The two slides 9, 9' have second mechanical openings 20, 20', which run alongside the first mechanical openings 18, 18' at a distance, so that elastic webs 21, 21' for holding the movement journals 17, 17' in the slides 9, 9' without play are formed between the first and second mechanical openings 18, 18'; 20, 20'. The diameter of the movement journals 17, 17' is preferably slightly larger than the width of the first mechanical openings 18, 18', so that the elastic webs 21, 21' must yield elastically when the movement journals 17, 17' are inserted into the first mechanical openings 18, 18'. In this way, it is ensured that the movement journals 17,17' are held in the first mechanical openings 18, 18' without play.

Figure 3:
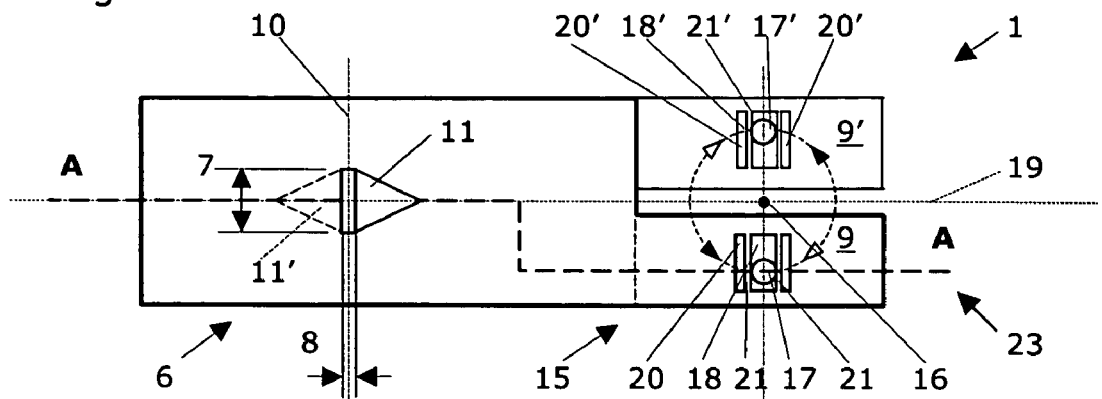
FIG. 3 shows a front view of a slit diaphragm according to the present invention in a second embodiment, having two slides positioned on two separate parallel lines for varying the slit width and/or the slit height in a first slide position, in which the two slides are essentially congruent to one another and define a specific slit width and a maximum slit height.
Figure 4:
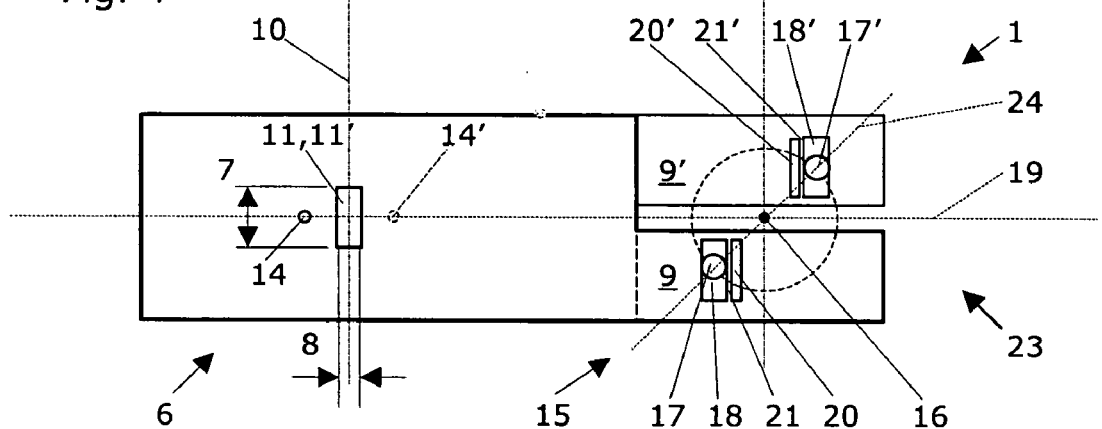
FIG. 4 shows a front view of a slit diaphragm according to the present invention in a third embodiment, having two slides positioned on two separate parallel lines for varying the slit width or the slit height in a first slide position, in which the two slides are essentially congruent to one another and define a maximum slit width at a first slit height.

The motor drive 15 preferably includes a stepping motor having a reduction gear (not shown), as well as a rotating disk 22, on which the movement journals 17, 17', which engage in the first mechanical openings 18, 18' of the slides 9, 9', are positioned in such a way that they lie, in a first slide position 23, on a line 24 which extends through the axis of rotation 16 and runs at an angle of 90° to the movement direction 19 of the slides 9, 9' (cf. FIGS. 2 and 3) or deviating therefrom (cf. FIG. 4).

In a second slide position (cf. FIG. 2B), the two slides 9, 9' are moved somewhat toward one another, so that a middle slit width 8 results at a first slit height 7, which remains the same. This slide position is reached by rotating the rotating disk 22 slightly using the motor 15.

In a third slide position (cf. FIG. 2C), the two slides 9, 9' are moved more toward one another, so that a minimum slit width 8 results at a first slit height, which still remains the same.

In a fourth slide position (cf. FIG. 2D), the two slides 9, 9' are moved further toward one another, so that now the two further optical openings 14, 14', which are positioned diametrically opposing at a distance to the optical openings 11, 11', lie precisely one over another and a fixed slit width having a second, reduced slit height results. The slit width of this slit having the second, reduced slit height may also be varied through a slight further or reverse movement of the slides 9, 9'.

It is obvious that, with progressing rotation of the rotating disk 22, the movement journals 17, 17' move in the first mechanical openings 18, 18' of the slides 9, 9' more and more toward the movement direction 19 shown as the axis of symmetry. In order to allow this movement, the first mechanical openings 18, 18' in the two slides 9, 9' are oblong and are each positioned perpendicularly to the movement direction 19 of the slides 9, 9'.

FIG. 3 shows a front view of a slit diaphragm according to the present invention in a second embodiment, having two slides positioned on two separate parallel lines for varying the slit width and/or slit height, in a first slide position, in which the two slides are essentially congruent to one another and define a specific slit width and a maximum slit height. The optical openings 11, 11' in the two slides 9, 9' have a pentagonal shape and are mirror-symmetric to one another here. Through a slight rotation of the rotating disk 22 using the motor drive 15 in the counterclockwise direction (solid arrow tip) around the center of rotation 16, the slides 9, 9' are moved toward one another in such a way that the slit height 7 remains unchanged, but the slit width 8 is reduced (similarly to FIG. 2). By rotating the rotating disk 22 using the motor drive 15 counterclockwise (empty arrow tip) around the center of rotation 16, the slides 9, 9' are moved toward one another in such a way that the slit height 7 is reduced and the slit width 8 increases.

If this increase of the slit width 8 is not desired—according to a fourth embodiment of the slit diaphragm according to the present invention—a third slide 9''', positioned on a further separate, parallel line, having a narrow optical opening 11'' which defines a fixed slit width 8, may be positioned symmetrically to the optical axis in such a way (cf. FIG. 5) that with increasing movement of the rotating disk 22 clockwise, the slit height 7 may be varied while the slit width now remains the same.

FIG. 4 shows a front view of a slit diaphragm according to the present invention in a third embodiment, in which the movement journals 17, 17' fixed on the rotating disk 22, which engage in the first mechanical openings 18, 18' of the slides 9, 9', are positioned in such a way that they lie, in a first slide position 23, on a line 24, which extends through the axis of rotation 16 and runs at an angle of 45° to the movement direction 19 of the slides 9, 9'. This arrangement has the advantage that a larger movement of the rotating disk 22 is necessary for a comparable slide movement, i.e., the slide movement may be controlled even more precisely.

These two slides positioned on two separate parallel lines are also suitable for varying the slit width or the slit height. Notwithstanding the other embodiments shown, the two slides 9, 9' have second mechanical openings 20, 20', which do not run on both sides along the first mechanical openings 18, 18', so that an elastic web 21, 21' for holding the movement journals 17, 17' in the slides 9, 9' without play is formed between the first and second mechanical openings 18, 18'; 20, 20' only on the right or only on the left in each case.

FIG. 5 shows a sectional illustration of a slit diaphragm 6 according to the present invention in the fourth embodiment. The corresponding sectional line is identified in FIG. 3 with A—A. Three slides 9, 9', 9''' positioned on three separate parallel lines are located in a first slide position, in which the two slides 9, 9' are essentially congruent to one another and define a first slit width 8 at a maximum slit height. This slit width 8 may be determined through the movement of the slides 9, 9' or even by adding the slide 9'''; in this case, this addition maybe performed automatically and/or driven by a motor. Light of the light source 2, which is located on optical axis 10, penetrates the slit diaphragm and impinges on a field 3 defined by the slit diaphragm 6, which is the surface of a sample 5 located in a well 44 of a microplate 43 here. This sample is penetrated by the excitation light, so that detectors (not shown) positioned physically or at least functionally in the optical axis may detect the light triggered and/or reflected or scattered by the sample.

The motor drive 15 for moving the two slides 9, 9', which includes two movement journals 17, 17' pivotable symmetrically around the axis of rotation 16, may also be seen especially well in FIG. 5. The movement journal 17 shown here engages in the first mechanical opening 18 in the slide 9. This first mechanical opening 18 is separated here from the second mechanical opening 20 running parallel by an elastic web 21 on both sides. The movement journal 17 is thus held elastically and without play on both sides in the slide 9.

The slides 9, 9', 9''' are preferably made of spring steel, especially preferably thin spring sheet steel, and are preferably matte black at least in the region of the optical openings 11, 11', 11''; 14, 14'. The cutting out of the slides and/or the implementation of the openings 11, 11', 11''; 14, 14'; 18, 18'; 20, 20' is preferably performed through etching or laser cutting. Using the same construction to manufacture the two slides 9, 9', which may then be assembled mirror-reversed into a slit diaphragm 6, is especially preferable and cost-effective.

Figure 6:
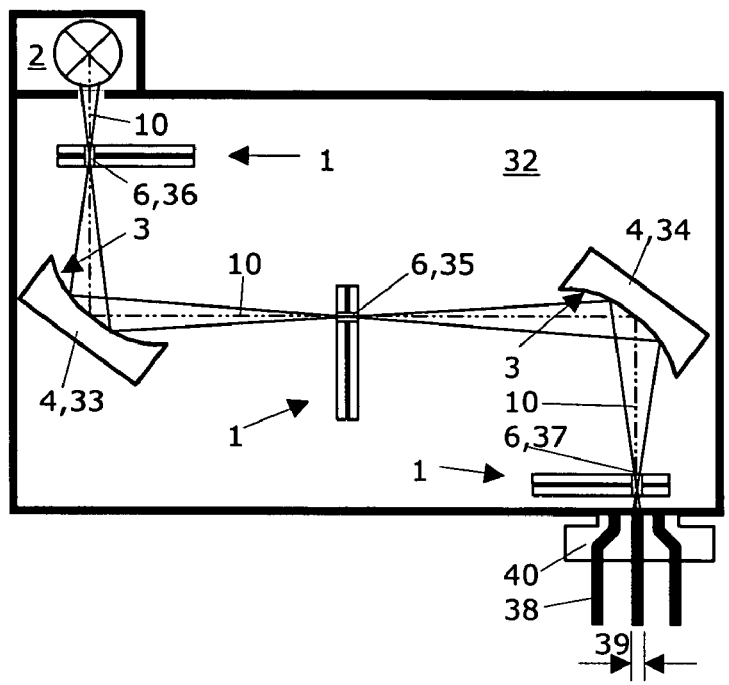
FIG. 6 shows a partial section through a monochromator including three slit diaphragms for a system for measuring the fluorescence and/or luminescence and/or absorption of samples irradiated with the light from a light source.

FIG. 6 shows a partial section through a monochromator 32, including three slit diaphragms 6, for a system 31 for measuring the fluorescence and/or luminescence and/or absorption of samples 5 irradiated with the light from a light source 2. In this case, light from the light source 2 enters along the optical axis 10 through the slit diaphragm 6 defining the entry slit 36 of a first device 1 and is incident on a field 3 of an optical element 4 in the form of a first grating 33. The light is reflected on this first grating 33, enters along the optical axis 10 through the slit diaphragm 6 defining the middle slit 35 of the second device 1 and is incident on a field 3 of an optical element 4 in the form of a second grating 34. The light is reflected at this second grating 34, enters along the optical axis 10 through the slit diaphragm 6 defining the exit slit 37 of a third device 1 and is incident on an optical fiber and/or an optical fiber bundle 38 having a specific diameter 39. This optical fiber and/or this optical fiber bundle 38 conduct the now monochromatic light to a sample 5 (cf. FIG. 7).

In an additive double monochromator, the gratings are positioned so that the dispersions of the two gratings 33, 34 add. The spectrum produced by the first monochromator is split even further by the second monochromator. In the subtractive monochromator, the gratings are positioned so that the dispersions of the two gratings 33, 34 subtract.

For application, this means that the total dispersion of a subtractive monochromator is given by the dispersion of the first monochromator and is therefore only half as large as that of an additive monochromator. The second monochromator of a preferred, subtractive setup therefore merely has the purpose of improving the scattered light suppression. At a given slit width 8, a subtractive monochromator therefore advantageously produces light having a doubled spectral bandwidth and therefore more energy. As a further advantage of a subtractive monochromator, is to be noted that it is sufficient to move the entry slit and middle slit of the monochromator to set the bandwidth; the exit slit may have a fixed width, due to which a simpler mechanism may be used.

Figure 7:
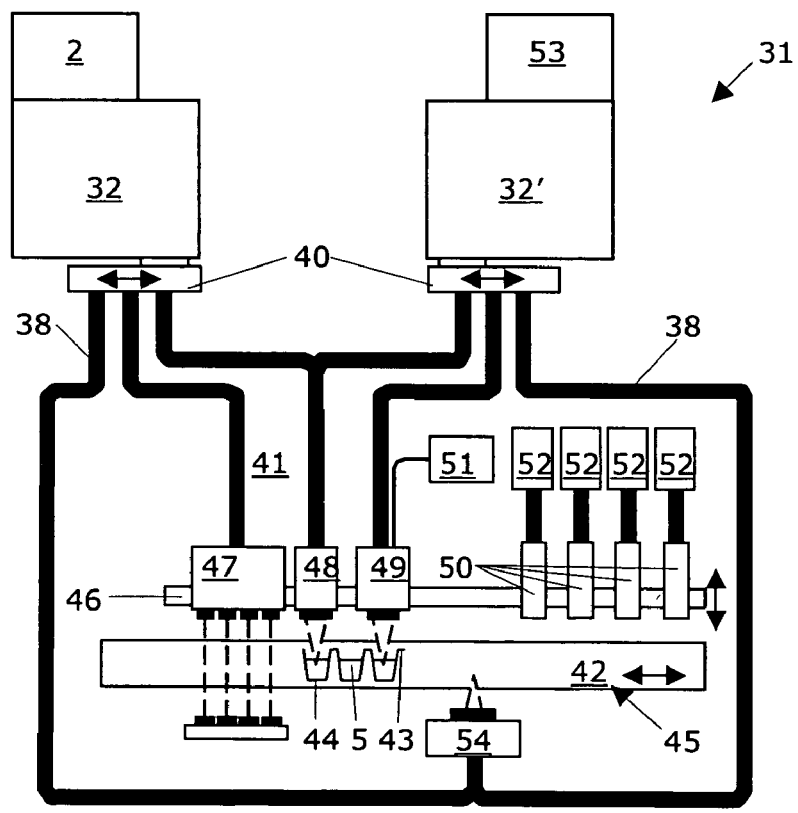
FIG. 7 shows a schematic layout of a system, constructed as a multifunction reader for measuring the fluorescence and/or luminescence and/or absorption of samples irradiated with the light from a light source, having an excitation monochromator and an emission monochromator as shown in FIG. 6.

FIG. 7 shows a schematic layout of a system 31, constructed as a multifunction reader, for measuring the fluorescence and/or luminescence and/or absorption of samples 5 irradiated with the light from a light source 2 having an excitation monochromator 32 and an emission monochromator 32', according to the construction principle in FIG. 6. The left monochromator 32 is like the transmitter (flashlamp 2 having settable wavelength and bandwidth), the right monochromator 32' functions as a detector 53 having settable wavelength and bandwidth. Light source, samples 5, and detector 53 (photomultiplier=PMT) are optically connected to one another via a fiber-optic system 41, the individual paths, i.e., optical fibers and/or optical fiber bundles 38, may be selected using fiber slides 40.

In this exemplary system 31, the following components are seated on a vertically movable (see double arrow) optic holder 46:

a 1-channel to 4-channel optic 47 for absorption measurements;
"top" optics 48, 49 for measuring the fluorescence intensity;
"top" optics 50 for measuring the luminescence intensity; LED light source;
photon-counting detectors 51, 52 which are preferably implemented as PMT.

Below the holder 42 for microplates 43, which is displaceable in the X and Y directions in a horizontal plane 45, a "bottom" optic 54 is located here for measuring the fluorescence intensity which originates from the samples 5 located in the wells 44.

For a given size of a well 44, the diameter 39 of the fiber bundle illuminating the well and/or the optical fiber 38 illuminating the well has an upper limit in principle. The width of the fiber bundle on the monochromator side then also has an upper limit at a given slit height 7. The slit width 8 of the exit slit 37 and thus the achievable bandwidth are therefore also limited. In a subtractive monochromator, double the bandwidth is obtained at the same slit width 8 and therefore twice as much energy may be incident in the well to be measured at a given fiber geometry (the diameter is defined by the well size, as noted above).

Any arbitrary combinations of the features disclosed are included in the scope of the present invention. The reference numbers each refer to corresponding features, even when reference is not expressly made thereto in every case.

What is claimed is:

1. A device for delimiting a fixed field on the surface of an optical element or a sample impinged with light from a fixed light source, the device having a slit diaphragm, including a slit height and a slit width, which includes first and second linearly movable slides, positioned parallel to one another on two separate parallel lines, which are movable at least partially symmetrically to one another in relation to a fixed optical axis that is defined by the light source, the slit diaphragm, and the field on the surface of the optical element or the sample, each of the two slides including at least one optical opening, which—for continuous adjustment of at least the slit height or the slit width—are positioned at least partially on the optical opening of the neighboring slide in the region of the optical axis, wherein the device includes a motor drive with a motor having an axis of rotation for moving the two slides in a movement direction, wherein the axis of rotation of the motor is positioned perpendicularly to the movement direction, wherein the motor drive for moving the two slides includes two movement journals positioned on a rotating disk and pivotable symmetrically around the axis of rotation of the rotating disk, wherein each of the movement journals engages a first mechanical opening provided on each slide, and each slide being cut from a piece of suitable steel sheet.

2. The device according to claim 1, wherein the optical openings in the two slides have shapes which are identical to one another or are mirror symmetric.

3. The device according to claim 2, wherein the optical openings in the two slides have a rectangular shape to produce a variable slit width at a constant slit height.

4. The device according to claim 2, wherein the optical openings in the two slides have a pentagonal shape to produce a variable slit width at a constant slit height or a variable slit height at a variable slit width.

5. The device according to claim 4, wherein a third slide is positioned parallel to the two slides and includes a narrow optical opening, which is positioned, in the region of the optical axis, at least partially on the optical openings of the two slides and is itself symmetrical to this optical axis.

6. The device according to claim 1, wherein the first slide, to produce a variable slit height, includes an optical opening which has a pentagonal shape and a second slide includes an optical opening which has a narrow rectangular shape.

7. The device according to claim 1, wherein the two slides include further optical openings, which are positioned to be one on top of another and have rectangular or round shapes which are identical to one another.

8. The device according to claim 1, wherein the slides are matte black at least in the region of the optical openings.

9. The device according to claim 1, wherein the first mechanical openings in the two slides are oblong and are each positioned perpendicularly to the movement direction of the slides.

10. The device according to claim 9, wherein the two slides have second mechanical openings, which run alongside the first mechanical openings at a distance, so that elastic webs, for holding the movement journals in the slides without play, are formed between the first and second mechanical openings.

11. The device according to claim 1, wherein the motor drive includes a rotating disk, on which the movement journals engaging in the first mechanical openings of the slides are positioned in such a way that, in a first slide position, movement journals lie on a line which extends through the axis of rotation and runs at an angle of 90° to the movement direction of the slides.

12. The device according to claim 9, wherein the motor drive includes a rotating disk, on which the movement journals engaging in the first mechanical openings of the slides are positioned in such a way that, in a first slide position, movement journals lie on a line which extends through the axis of rotation.

13. The device according to claim 10, wherein the motor drive includes a rotating disk, on which the movement journals engaging in the first mechanical openings of the slides are positioned in such a way that, in a first slide position, movement journals lie on a line which extends through the axis of rotation.

14. The device according to claim 1, wherein the axis of rotation of the rotating disk is identical to the axis of rotation of the motor.

15. The device according to claim 1, wherein the slides are made of spring sheet steel.

16. A system for measuring at least one of the signals, selected from the group of fluorescence, luminescence, and absorption, from samples irradiated with the light from a light source, the system including at least one monochromator or a spectrometer having optical elements, which includes at least one device according to claim 1.

17. The system according to claim 16, which includes at least one optic that is implemented so it is moved essentially perpendicularly to the plane in the Z direction toward samples held in the system.

18. The system according to claim 16, wherein the optical elements of the monochromator include a first and second grating, between which a slit diaphragm for producing a middle slit is positioned.

19. The system according to claim 18, wherein the optical elements of the monochromator include a slit diaphragm, positioned upstream from the first grating, to produce an entry slit, and a slit diaphragm, positioned downstream from the second grating, to produce an exit slit.

20. The system according to claim 18, wherein at least one optical fiber having a diameter is connectable at the exit slit of the monochromator.

21. The system according to claim 20, which includes two monochromators, at each of whose entry or exit slits a fiber slider is positioned, to which at least two optical fibers of a fiber-optic system are connectable.

22. The system according to claim 16, which includes a holder for holding microplates, in whose wells samples are positioned.

23. The system according to claim 22, wherein the holder having one or more microplates is movable in a targeted way in an essentially horizontal plane in an X direction and in a Y direction running perpendicularly thereto.

24. A method for delimiting a fixed field on the surface of an optical element or a sample impinged with light from a fixed light source, in which a device having a slit diaphragm is used, of which at least the slit height or the slit width is continuously adjustable, comprising setting the slit width of the slit diaphragm, using first and second slides positioned parallel to one another, by moving the two slides linearly at least partially symmetrically to one another in relation to a fixed optical axis that is defined by the light source, the slit diaphragm, and the field on the surface of the optical element or the sample, until a desired slit is obtained through at least partial overlap of optical openings positioned in each slide in the region of the optical axis, and wherein the two slides of the device are moved in a movement direction using a motor drive with a motor, the motor having an axis of rotation which is positioned perpendicularly to the movement direction, wherein moving the slides with the motor drive includes pivoting two movement journals symmetrically around the motor axis of rotation, the movement journals each engaging a first mechanical opening on the two slides, each slide being cut out in one piece from a suitable steel sheet.

\* \* \* \* \*